United States Patent [19]
Dou et al.

[11] Patent Number: 5,481,113
[45] Date of Patent: Jan. 2, 1996

[54] APPARATUS AND METHOD FOR MEASURING CONCENTRATIONS OF COMPONENTS WITH LIGHT SCATTERING

[75] Inventors: Xiaoming Dou; Harumi Uenoyama, both of Kyoto, Japan

[73] Assignee: Kyoto Daiichi Kagaku Co., Ltd., Kyoto, Japan

[21] Appl. No.: 284,213

[22] Filed: Aug. 2, 1994

[30] Foreign Application Priority Data

Aug. 5, 1993 [JP] Japan ..................... 5-194653

[51] Int. Cl.$^6$ ..................................... G01N 21/47
[52] U.S. Cl. .................... 250/341.1; 250/341.8; 356/301
[58] Field of Search ............ 250/339.11, 341.8, 250/341.1; 356/301

[56] References Cited

U.S. PATENT DOCUMENTS

| | | | |
|---|---|---|---|
| 4,427,889 | 1/1984 | Müller | 250/339.11 |
| 4,575,629 | 3/1986 | Schnell et al. | 356/301 X |
| 4,620,284 | 10/1986 | Schnell et al. | 356/301 X |
| 5,243,983 | 9/1993 | Tarr et al. | |
| 5,261,410 | 11/1993 | Alfano et al. | 356/301 X |
| 5,262,644 | 11/1993 | Maguire | |

FOREIGN PATENT DOCUMENTS

| | | | |
|---|---|---|---|
| 4-254744 | 9/1992 | Japan | |
| 92/10131 | 6/1992 | WIPO | |
| 9313402 | 7/1993 | WIPO | 250/341.1 |

OTHER PUBLICATIONS

Radziszewski et al., "Doubled Multiplexing in Fourier Transform Raman Spectroscopy", Applied Spectroscopy, vol. 44, No. 3, 1990, pp. 414–418.

"New Approach for Non–Destructive Sensing of Fruit Taste" *Sensors And Actuators B* pp. 447–450, May 1993 By Isao Taniguchi et al.

"Near–Infrared Raman Spectroscopy with a 783–nm, Diode Laser" *Applied Spectroscopy*, vol. 43, No. 3, pp. 372–375, 1989 By J. M. Williamson et al.

Patent Abstracts of Japan, vol. 18, No. 18, P–1673, JP 52–56782, Jan. 1994.

"New Approach for Non–Destructive Sensing of Fruit Taste" Isao Taniguchi (Applied Electronics Research Center), 4B02, pp. 514–517.

*Primary Examiner*—Carolyn E. Fields
*Assistant Examiner*—Edward J. Glick
*Attorney, Agent, or Firm*—Birch, Stewart, Kolasch & Birch

[57] ABSTRACT

An apparatus and a method for measuring concentrations of components with light scattering allows measurement of concentrations of components in a measuring object to be accomplished in non-destructive fashion by using light in near-infrared wavelength ranges with good transmissivity and relatively low light quantum energy. The apparatus is composed of a light irradiator (1) for irradiating excited light in a near-infrared wavelength range to a measuring object (16), a photodetector (2) for receiving and spectrally separating Raman scattered light derived from the measuring object (16), and an arithmetic unit (3) for calculating concentration of a component in the measuring object (16) from intensity of the Raman scattered light and outputting a calculation result.

4 Claims, 5 Drawing Sheets

APPARATUS AND METHOD FOR MEASURING CONCENTRATIONS OF COMPONENTS WITH LIGHT SCATTERING

BACKGROUND OF THE INVENTION

1. Field of the Invention

The present invention relates to an apparatus and a method for measuring concentrations of components with light scattering, in which the concentrations of the components in an object are measured in non-destructive fashion by making use of Raman scattered light.

2. Description of the Prior Art

Conventionally, there has been known an apparatus for measuring concentrations of components in citrus fruits in non-destructive fashion by making use of Raman scattered light (Japanese Patent Laid-Open Publication No. 4-254744 (1992)).

This apparatus is so arranged that laser of a wavelength in visible radiation range (e.g. wavelength: 514.5 nm) is irradiated to a citrus fruit and, taste of the citrus fruit is determined, based on the intensity of Raman scattered light generated due to carotenoid contained in the pericarp of the citrus fruit. Further, the saccharic acid ratio of the citrus fruit is estimated from the content of carotenoid contained in the pericarp of the citrus fruit so as to judge the taste.

In the above conventional apparatus, laser of a wavelength in visible radiation range is used to calculate the content of carotenoid contained in the pericarp of a citrus fruit, which is the measuring object. The laser of a wavelength in visible radiation range is low in transmissivity when it is applied to the measuring object, and large in attenuation factor due to absorption and scattering in the measuring object. Therefore, it could be considered that, in the above apparatus, the content of carotenoid contained in the fruit is estimated by measuring the quantity of Raman scattered light derived not from the fruit itself but from its pericarp, i.e. its surface layer, so as to judge the taste of the citrus fruit.

Further, laser of a wavelength in visible radiation range has large quantum energy, as compared with laser in near-infrared wavelength range.

As a result, when the measuring object is a living body such as in clinical medicine tests, such a problem arises that use of the laser in a wavelength in visible radiation range that will reach a measurement site within the living body would result in destruction of structures in the living body.

Further, when the laser of a wavelength in visible radiation range is irradiated to measure concentrations of components in the measuring object, such further problems arise that Raman spectroscopy on the living body by laser excitation in the visible radiation range would involve generation of fluorescence from the living body as well as a more frequent occurrence of photolysis, i.e. photochemical reaction.

The fluorescence and photochemical reaction are likely to be produced by the following cause.

In the case of the conventional laser excitation in the visible wavelength range, the energy of a light quantum is high relative to targeted transition energy, such that electrons can be excited not only to a vibrational level that causes a targeted Raman scattered light to be generated, but also to a high energy level of different electron state. Therefore, it is considered that when Raman scattering occurs due to transition between energy levels, an excitation to high energy level also occurs, which results in fluorescence generation. As a consequence of this, a more intense background signal of Raman spectrum results, making the measurement of spectrum difficult to achieve.

It is considered that the photochemical reaction would occur due to the relatively high energy of light quantum of the laser of a wavelength in visible radiation range. Namely, it is considered that after absorption of energy of the laser by a substance, its molecular structure would vary, thus resulting in the photochemical reaction. As a result, the structure of the measuring object would be damaged as viewed microscopically, so that the analysis would no longer be a non-destructive analysis in a strict sense. In particular, when laser Raman spectroscopy is applied to analysis of living bodies or foods, the above problem would be clearer because these substances in many cases contain components that are complex and easily subject to photolysis.

SUMMARY OF THE INVENTION

The present invention has been accomplished to solve such conventional problems. Accordingly, the object of the present invention is to provide an apparatus and a method for measuring concentrations of components with light scattering, which makes it possible to measure concentrations of components in a measuring object in non-destructive fashion by using light in a wavelength range with good transmissivity, a weak background signal caused by fluorescence, no occurrence of photochemical reaction, and low energy.

To achieve the above object, as a first aspect of the present invention, there is provided an apparatus for measuring concentrations of components with light scattering, comprising a light irradiator for irradiating excited light in a near-infrared wavelength range to a measuring object, a photodetector for receiving and spectrally separating Raman scattered light derived from the measuring object, and an arithmetic unit for calculating concentration of a component in the measuring object from intensity of the Raman scattered light and outputting a calculation result.

As a second aspect of the present invention, the aforementioned light irradiator is a laser generator.

As a third aspect of the present invention, the aforementioned component is glucose and the Raman scattered light has a wave number of 1090 to 1150 $cm^{-1}$.

As a fourth aspect of the present invention, the aforementioned component is glucose and the Raman scattered light has a wave number of 2850 to 3000 $cm^{-1}$.

As a fifth aspect of the present invention, there is provided a method for measuring concentrations of components with light scattering, comprising a step for irradiating excited light in a near-infrared wavelength range from a light irradiator to a measuring object, a step for receiving and spectrally separating Raman scattered light derived from the measuring object by a photodetector, and a step for calculating concentration of a component in the measuring object from intensity of the Raman scattered light and outputting a calculation result by an arithmetic unit.

With the above arrangement, it becomes feasible to measure concentrations of components directly from the Raman scattered light derived from the inside of the measuring object without destroying the internal structure of the measuring object.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Hereinbelow, an embodiment of the present invention is described with reference to the accompanying drawings.

Figure 1:
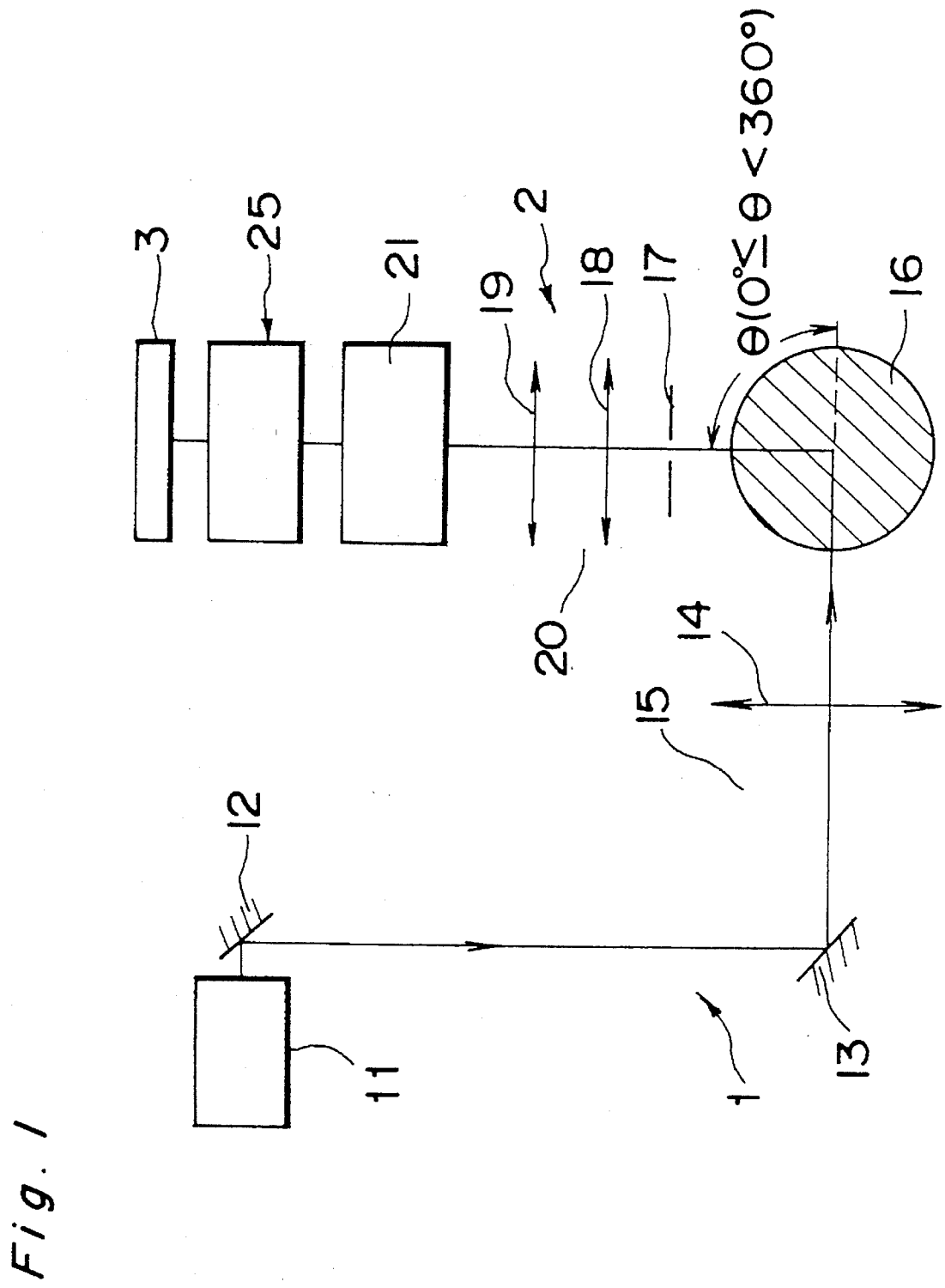
FIG. 1 is a view outlining the arrangement of the apparatus for measuring concentrations of components with light scattering according to a first embodiment of one aspect of the present invention, to which certain methods for measuring concentrations of components with light scattering of another aspect of the present invention are applied.

FIG. 1 illustrates an apparatus for measuring concentrations of components with light scattering according to a first embodiment of the first, second, third, and fourth aspects of the present invention, to which the method for measuring concentrations of components with light scattering according to the fifth aspect of the present invention is applied. The apparatus comprises a light irradiator 1, a photodetector 2, and an arithmetic unit 3.

The light irradiator 1 is composed of a laser generator 11 and an optical system 15 having two reflection mirrors 12, 13 and a convex lens 14. Laser in a near-infrared wavelength range is generated by the laser generator 11. The laser is reflected by each of the reflection mirrors 12, 13 and converged onto a measuring object 16 by the convex lens 14. In this arrangement, optical axis alignment of the laser with respect to the measurement object 16 can be accomplished by controlling the angle and position of the two reflection mirrors 12, 13.

The photodetector 2 is composed of an optical system 20 having a filter 17 and two convex lenses 18, 19, a spectrometer 21, and a detector 25. The filter 17 functions to transmit only Raman scattered light in near-infrared wavelength ranges from within the measuring object 16, for example, Raman scattered light with wave number 1090 to 1150 $cm^{-1}$ and 2850 to 3000 $cm^{-1}$, and to cut off light of the other wavelengths. Also, the light that has transmitted through the filter 17 is converged onto the spectrometer 21 by the two convex lenses 18, 19 and detected by the detector 25.

In the arithmetic unit 3, Raman scattered light of a predetermined wavelength that has transmitted through the filter 17 is spectrally separated into components by the spectrometer 21, and based on the intensity detected by the detector 25, the concentration of a component in the measuring object 16 is calculated and the calculation result is outputted. For example, Raman scattered light with wave number 1090 to 1150 $cm^{-1}$ and 2850 to 3000 $cm^{-1}$ is spectrally separated into components by the spectrometer 21, and based on the intensity detected by the detector 25, the concentration of glucose in the measuring object 16 is calculated and the calculation result is outputted.

Assuming that the angle formed by the scattered light derived from the measuring object 16 against the incident light is $\theta$, the angle $\theta$ is set at 90° in this embodiment. However, the angle is not limited to 90°, but may assume an arbitrary value ranging from 0° to 360° ($0° \leq \theta < 360°$).

Next described is the method for measuring concentrations of components with light scattering according to the fifth aspect of the present invention which is applied to the apparatus having the above arrangement.

At the first step, with the measuring object 16 in regular position as shown in FIG. 1, laser in near-infrared wavelength ranges is irradiated from the light irradiator 1 to the measuring object 16.

At the second step, Raman scattered light derived from the measuring object 16, for example Raman scattered light with wave number 1090 to 1150 $cm^{-1}$ and 2850 to 3000 $cm^{-1}$ is spectrally separated into components by the photodetector 2, more specifically by the spectrometer 21 via the optical system 20, and received by the detector 25, where its intensity is detected.

At the third step, the concentration of a component, e.g. glucose, in the measuring object 16 is calculated from the intensity of the Raman scattered light and the calculation result is outputted by the arithmetic unit 3.

The measuring object 16 is exemplified by living bodies, separated or extracted matters from living bodies, i.e., blood, urine, feces, saliva, lachrymal liquid, bacteria, and breathing gas, as well as foods, fruits, grains, and rubbers. The components in the measuring object 16 are exemplified by haemoglobin, albumin, protein, lipid, bilirubin, ketone body, enzymes, hormones, and the like in addition to the aforementioned glucose.

Figure 2:
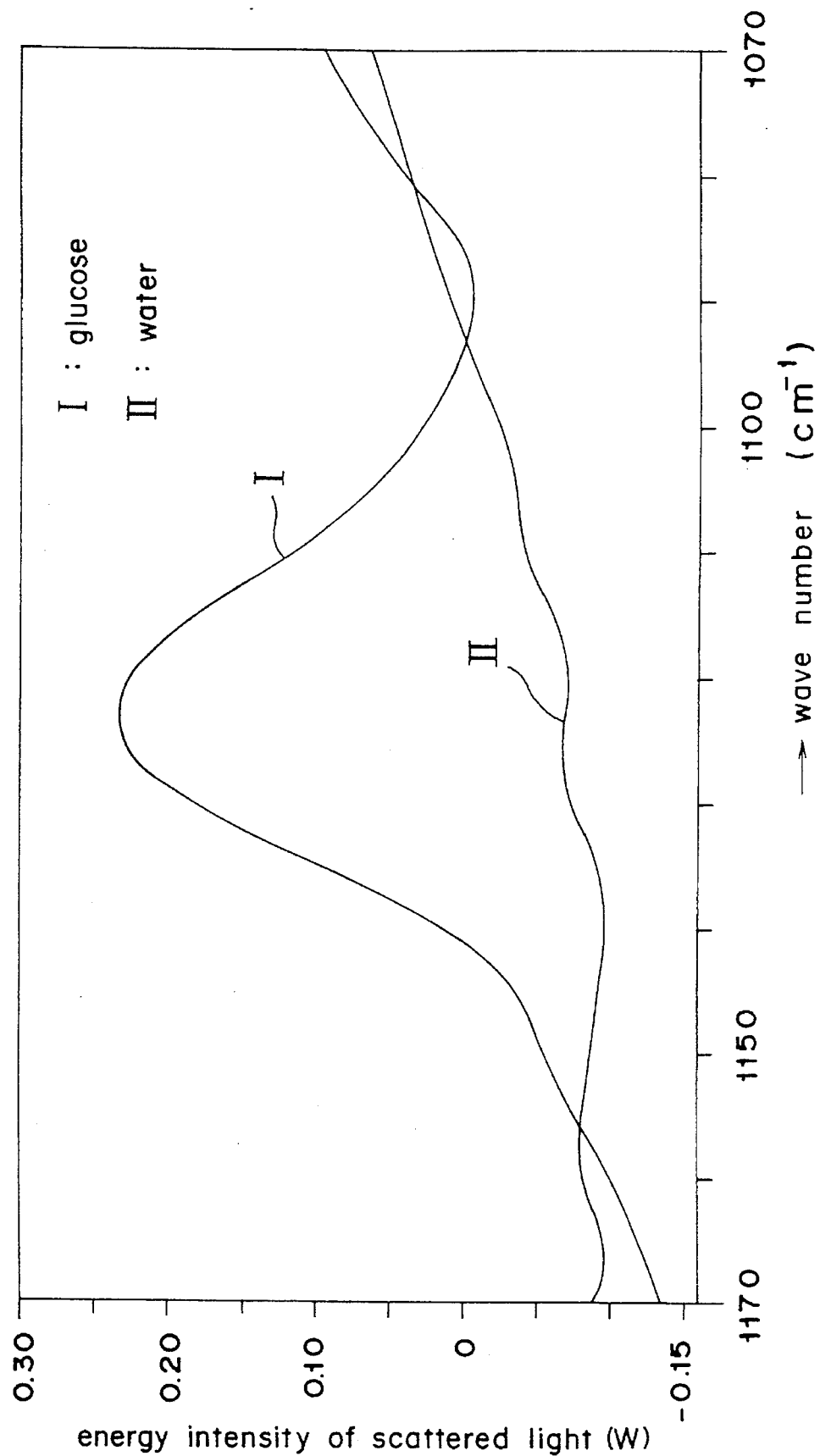
FIG. 2 is a view showing Raman spectrum of the Raman scattered light derived from glucose in a glucose aqueous solution.
Figure 3:
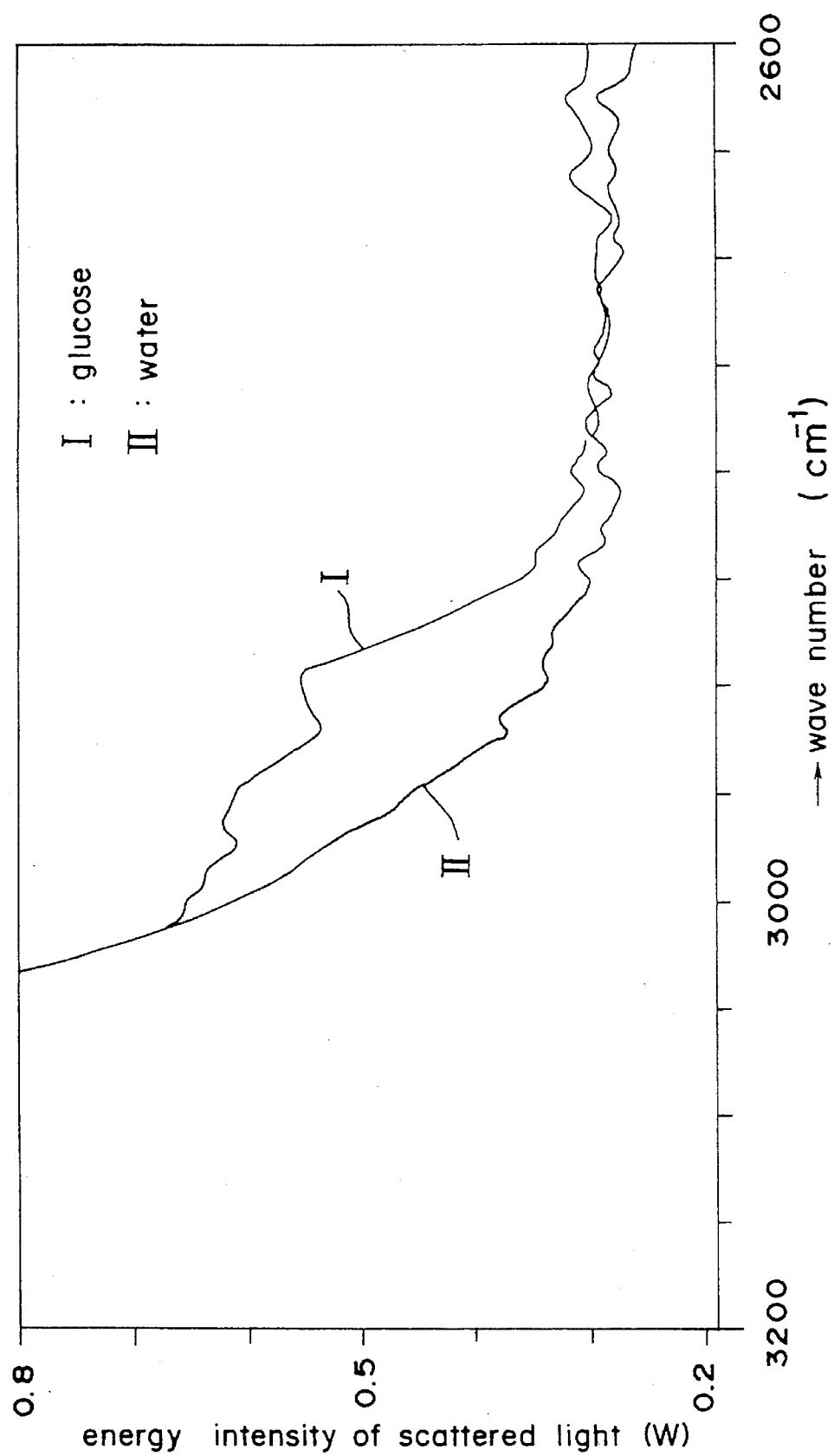
FIG. 3 is a view showing Raman spectrum of the Raman scattered light derived from glucose in a glucose aqueous solution.

FIGS. 2 and 3, where the abscissa represents wave number ($cm^{-1}$) and the ordinate represents energy intensity of scattered light (W), show results of measuring the intensity of scattered light by the apparatus shown in FIG. 1 with the measuring object 16 being a glucose aqueous solution, in which case there exist bands due to the Raman scattered light derived from glucose in the wave number ranges of 1090 to 1150 $cm^{-1}$ and 2850 to 3000 $cm^{-1}$. These bands have been unknown so far, and have been newly found as a result of measuring the spectrum of the scattered light derived from the measuring object 16 in the wave number range of 4000 to 400 $cm^{-1}$. More specifically, there have been observed a band of Raman scattered light due to C—C group stretching vibration and C—H group deformation vibration of functional groups of carbohydrates in the vicinity of wave number 1123 $cm^{-1}$, and another band of Raman scattered light due to C—H group stretching vibration and $CH_2$ group stretching vibration of functional groups of carbohydrates in the vicinity of wave number 2900 cm$^{-1}$ and 2965 cm$^{-1}$.

Figure 4:
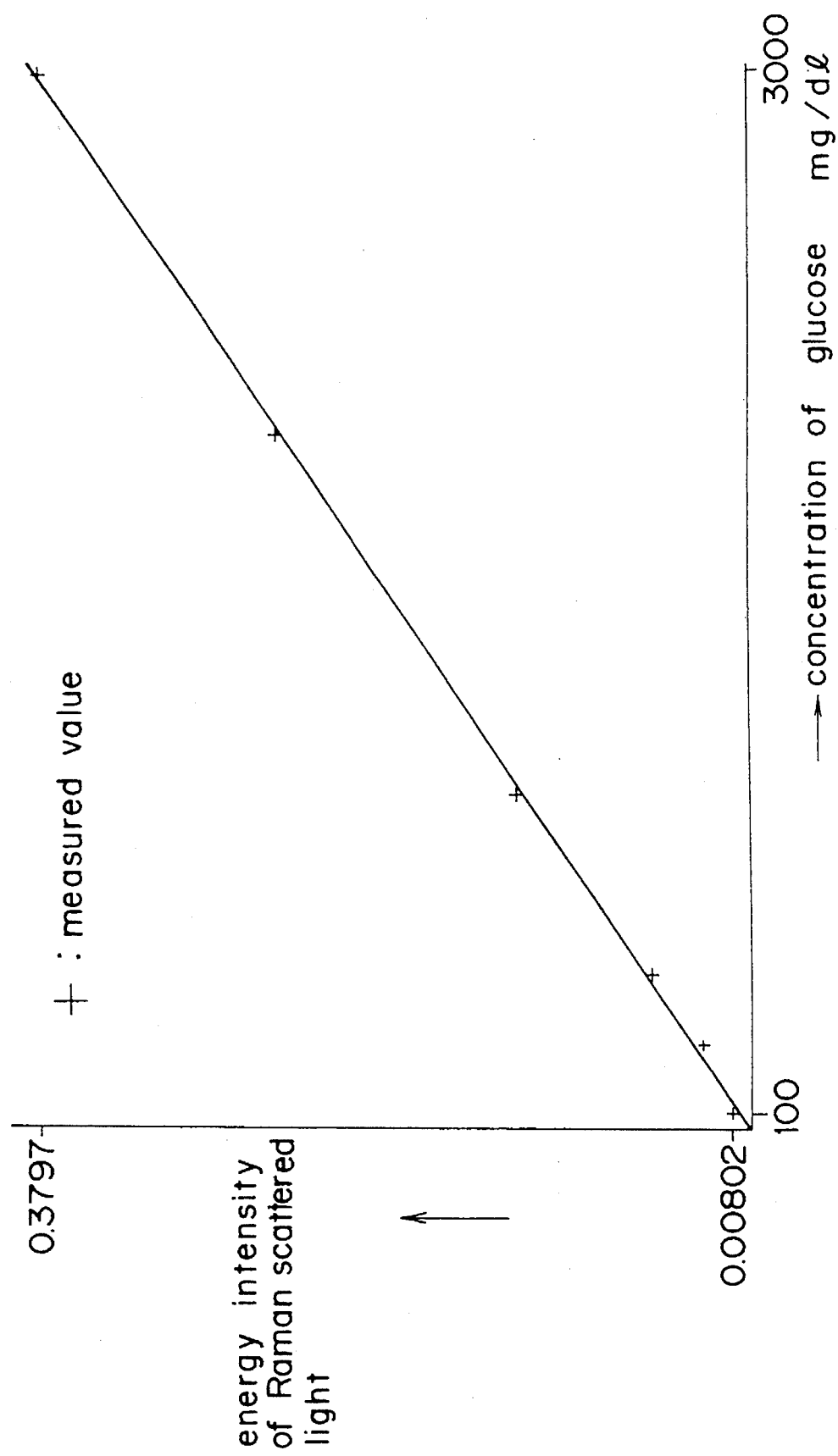
FIG. 4, where the abscissa represents the glucose concentration (mg/dl) and the ordinate represents energy intensity of light (W), is a view showing measurement results (marked +) as to the relation between glucose concentration and intensity of Raman scattered light with wave number 1123 $cm^{-1}$ as well as a line determined by the method of least square based on data of the measurement results.

FIG. 4, where the abscissa represents glucose concentration (mg/dl) and the ordinate represents energy intensity of Raman scattered light (W), shows measurement results (marked +) as to the relation between glucose concentration and intensity of Raman scattered light with wave number 1123 cm$^{-1}$ as well as a line determined by the method of least square based on data of the measurement results, in which case there exists a constant correlation between glucose concentration and the intensity of Raman scattered light.

In the above embodiment, laser in near-infrared wavelength ranges with superior transmissivity and small light energy is applied to the measuring object 16 in non-destructive fashion, and based on the intensity of Raman scattered light derived from the measuring object 16, concentrations of components in the measuring object 16 are measured in non-destructive fashion. Also, as exemplified by glucose in FIG. 4, there is a constant relation between the concentrations of components and the intensity of Raman scattered light. As a result, light reaches a measurement site within the measuring object 16, and the Raman scattered light derived from this site allows direct, correct measurement of concentrations of components. When Raman scattered light is used for measurement of concentrations of components, intense fluorescence generated by the measuring object causes a great background signal to be issued, which would make an obstacle to correct concentration measurement. However, by using laser in near-infrared wavelength ranges at low quantum energy level, occurrence of fluorescence can be avoided, so that the S/N ratio is improved and therefore measurement accuracy can also be improved.

Also, light quantum energy is relatively lower in laser in near-infrared wavelength ranges than in visible ranges, making it more unlikely that the structures within the measuring object 16 will be damaged. Accordingly, the present invention can be applied to measurement of concentrations of components also in the medical and biological fields.

Further, spectral analysis for measurement of Raman scattered light with laser excitation in near-infrared wavelength ranges can be easily carried out. Therefore, the S/N ratio can be enhanced so that the measurement accuracy of concentrations of components can be improved.

Figure 5:
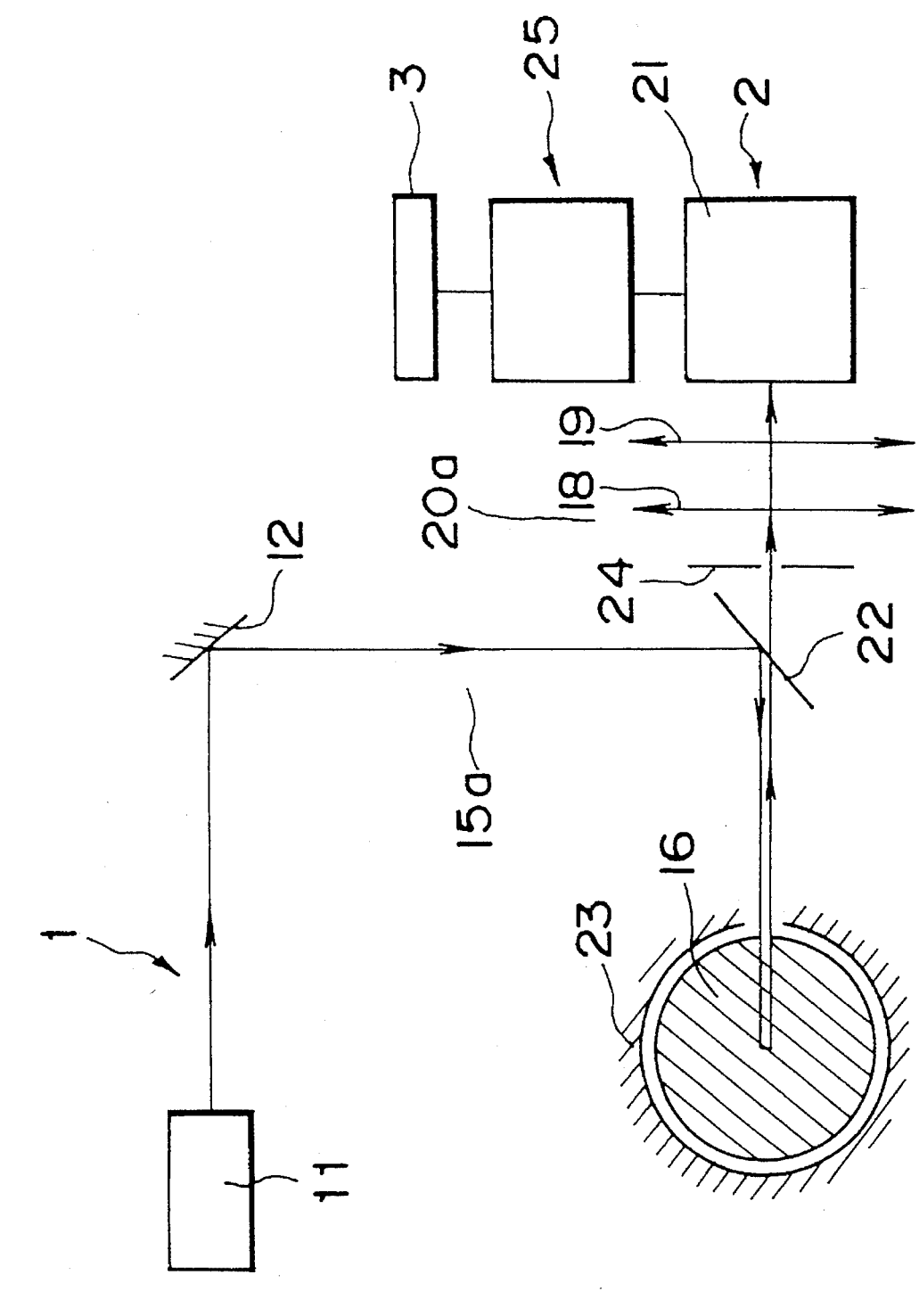
FIG. 5 is a view showing the outline of the apparatus for measuring concentrations of components with light scattering according to the second embodiment of one aspect of the present invention, to which certain methods for measuring concentrations of components with light scattering of another aspect of the present invention are applied.

FIG. 5 illustrates an apparatus for measuring concentrations of components with light scattering according to the second embodiment of the first, second, third, and fourth aspects of the present invention, to which a method for measuring concentrations of components with light scattering according to the fifth aspect of the present invention is applied. Like members common to the apparatus as shown in FIG. 1 are designated by like numerals and their description is omitted.

In the present embodiment, a light irradiator 1 is composed of a laser generator 11 and an optical system 15a having a reflection mirror 12 and a semi-transparent mirror 22. Incident laser is reflected by the reflection mirror 12 and the semi-transparent mirror 22 so that the laser is incident on a measuring object 16.

A photodetector 2 is composed of an optical system 20a having an integrating sphere 23, the semi-transparent mirror 22, a filter 24, and convex lenses 18, 19, and a spectrometer 21. The semi-transparent mirror 22 functions to transmit back Raman scattered light derived from the measuring object 16, leading the back Raman scattered light to the spectrometer 21 via the filter 24 and the convex lenses 18, 19, as in the first embodiment.

Then, concentrations of components in the measuring object 16 are calculated and calculation results are outputted by the arithmetic unit in the same way as in the first embodiment.

It is noted that the present invention is not limited to the above embodiment. For example, instead of the laser generator 11 of the light irradiator 1, such a high-luminance light source as a xenon lamp or a halogen lamp may also be used, and further a band-pass filter may be used in combination with the high-luminance light source.

Still further, instead of the spectrometer 21 of the photodetector 2, such a spectroscopic means as a diffraction grating or a band-pass filter and a quantity-of-light detection means may be used in combination.

As apparent from the above description, the apparatus for measuring concentrations of components with light scattering according to one aspect of the present invention comprises a light irradiator for irradiating excited light in a near-infrared wavelength range to a measuring object, a photodetector for receiving and spectrally separating Raman scattered light derived from the measuring object, and an arithmetic unit for calculating concentrations of components in the measuring object from intensity of the Raman scattered light and outputting calculation results.

Also, the method for measuring concentrations of components with light scattering according to another aspect of the present invention comprises a step for irradiating excited light in a near-infrared wavelength range from a light irradiator to a measuring object, a step for receiving and spectrally separating Raman scattered light derived from the measuring object by a photodetector, and a step for calculating concentration of a component in the measuring object from intensity of the Raman scattered light and outputting a calculation result by an arithmetic unit.

Thus, light reaches a measurement site within the measuring object, and the Raman scattered light derived from this site allows direct, correct measurement of concentrations of components. When Raman scattered light is used for measurement of concentrations of components, intense fluorescence generated by the measuring object causes a great background signal to be issued, which would make an obstacle to correct concentration measurement. However, by using laser in near-infrared wavelength ranges at low quantum energy level, occurrence of fluorescence can be avoided, so that the S/N ratio is improved and therefore measurement accuracy can be further improved. Also, laser in near-infrared wavelength ranges is relatively lower in energy, making it more unlikely that the structures within the measuring object will be damaged. Accordingly, the present invention can be applied to measurement of concentrations of components also in the medical and biological fields.

Further, spectral analysis for Raman spectroscopy with laser excitation in near-infrared wavelength ranges can be easily carried out. As a result, the S/N ratio can be enhanced and therefore the measurement accuracy of concentrations of components can also be advantageously improved.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An apparatus for measuring concentrations of components with light scattering, comprising:

a light irradiator for irradiating excited light in a near-infrared wavelength range to a measuring object;

a photodetector for receiving and spectrally separating Raman scattered light derived from the measuring object; and an arithmetic unit for calculating concentration of a component in the measuring object from intensity of the Raman scattered light and outputting a calculation result, wherein said component is glucose and said Raman scattered light has a wave number of 1090 to 1150 $cm^{-1}$.

2. The apparatus for measuring concentrations of components with light scattering according to claim 1, wherein said light irradiator is a laser generator.

3. An apparatus for measuring concentrations of components with light scattering, comprising:

a light irradiator for irradiating excited light in a near-infrared wavelength range to a measuring object;

a photodetector for receiving and spectrally separating Raman scattered light derived from the measuring object; and an arithmetic unit for calculating concentration of a component in the measuring object from intensity of the Raman scattered light and outputting a calculation result, wherein said component is glucose and said Raman scattered light has a wave number of 2850 to 3000 $cm^{-1}$.

4. The apparatus for measuring concentrations of components with light scattering according to claim 3, wherein said light irradiator is a laser generator.

* * * * *